United States Patent
Ni et al.

(10) Patent No.: US 7,189,204 B2
(45) Date of Patent: Mar. 13, 2007

(54) SLEEP DETECTION USING AN ADJUSTABLE THRESHOLD

(75) Inventors: Quan Ni, Saint Paul, MN (US); Zoe Hajenga, Minneapolis, MN (US); Douglas R. Daum, Oakdale, MN (US); Jeff E. Stahmann, Ramsey, MN (US); John D. Hatlestad, Maplewood, MN (US); Kent Lee, Fridley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 533 days.

(21) Appl. No.: 10/309,771

(22) Filed: Dec. 4, 2002

(65) Prior Publication Data

US 2004/0111041 A1 Jun. 10, 2004

(51) Int. Cl.
*A61B 5/02* (2006.01)
*A61B 5/00* (2006.01)
*A61B 5/08* (2006.01)

(52) U.S. Cl. .................... 600/300; 600/500; 600/529; 600/533; 600/538

(58) Field of Classification Search .................... None
See application file for complete search history.

(56) References Cited

U.S. PATENT DOCUMENTS

| | | | |
|---|---|---|---|
| 4,365,636 A | 12/1982 | Barker | |
| 5,485,851 A | 1/1996 | Erickson | |
| 5,814,087 A | 9/1998 | Renirie | |
| 5,861,011 A | 1/1999 | Stoop | |
| 6,091,973 A | 7/2000 | Colla et al. | |
| 6,128,534 A | 10/2000 | Park et al. | |
| 6,363,270 B1 | 3/2002 | Colla et al. | |
| 2001/0031930 A1* | 10/2001 | Roizen et al. | 600/544 |
| 2002/0193839 A1 | 12/2002 | Cho et al. | |
| 2003/0187336 A1* | 10/2003 | Odagiri et al. | 600/300 |
| 2004/0210155 A1* | 10/2004 | Takemura et al. | 600/534 |

FOREIGN PATENT DOCUMENTS

| | | |
|---|---|---|
| EP | 0 940 155 A | 9/1999 |
| EP | 1 317 943 A | 6/2003 |
| WO | WO 00/17615 | 3/2000 |

* cited by examiner

*Primary Examiner*—Robert L. Nasser
(74) *Attorney, Agent, or Firm*—Hollingsworth & Funk, LLC

(57) ABSTRACT

Devices and methods for sleep detection involve the use of an adjustable threshold for detecting sleep onset and termination. A method for detecting sleep includes adjusting a sleep threshold associated with a first sleep-related signal using a second sleep-related signal. The first sleep-related signal is compared to the adjusted threshold and sleep is detected based on the comparison. The sleep-related signals may be derived from implantable or external sensors. Additional sleep-related signals may be used to confirm the sleep condition. A sleep detector device implementing a sleep detection method may be a component of an implantable pulse generator such as a pacemaker or defibrillator.

63 Claims, 10 Drawing Sheets

SLEEP DETECTION USING AN ADJUSTABLE THRESHOLD

FIELD OF THE INVENTION

The present invention relates generally to sleep detection and, more particularly, to detecting sleep by adjusting a sleep threshold associated with a first sleep-related-signal using a second sleep-related signal.

BACKGROUND OF THE INVENTION

Sleep is generally beneficial and restorative to a patient, exerting great influence on the quality of life. A typical night's sleep for a normal person begins with a sleep stage known as slow wave sleep (SWS) characterized by low frequency electroencephalogram (EEG) activity. As the person falls asleep, brain activity declines and there is a progressive increase in the depth of sleep. At approximately ninety minute intervals, sleep lightens and a sleep stage known as rapid eye movement (REM) sleep is initiated. REM sleep is characterized by high frequency EEG activity, bursts of rapid eye movements, skeletal muscle atonia, and heightened autonomic activity.

There are typically 4–6 REM periods per night, with increasing duration and intensity toward morning. While dreams can occur during either REM or SWS sleep, the nature of the dreams varies depending on the type of sleep. REM sleep dreams tend to be more vivid and emotionally intense than SWS sleep dreams. Furthermore, autonomic nervous system activity is dramatically altered when REM sleep is initiated.

In patients with respiratory or heart disease, the brain during sleep can precipitate breathing disturbances, myocardial ischemia, or arrhythmia. Although REM sleep is a necessary component of normal sleep, serious consequences may be associated with both the increase in autonomic activity and the intense emotional responses that accompany dreaming in patients with cardiovascular disease or respiratory disorders, for example.

Disruptions of the respiratory system during sleep may include the conditions of sleep apnea or sleep hypopnea. Sleep apnea is a serious breathing disorder caused by airway obstruction, denoted obstructive sleep apnea, or derangement in central nervous system control of respiration, denoted central sleep apnea. Regardless of the type of apnea, people with sleep apnea stop breathing repeatedly during their sleep, sometimes hundreds of times a night and often for a minute or longer. Whereas sleep apnea refers to cessation of breathing, hypopnea is associated with periods of abnormally slow or shallow breathing. With each apnea or hypopnea event, the person generally briefly arouses to resume normal breathing. As a result, people with sleep apnea or hypopnea may experience sleep fragmented by frequent arousals.

An adequate quality and quantity of sleep is required to maintain physiological homeostasis. Prolonged sleep deprivation or periods of highly fragmented sleep ultimately will have serious health consequences. Chronic lack of sleep may be associated with various cardiac or respiratory disorders affecting a patient's health and quality of life.

SUMMARY OF THE INVENTION

The present invention is directed to detecting sleep. In one embodiment of the invention, a device for detecting sleep includes a first sensor for sensing a first sleep-related signal and a second sensor for sensing a second sleep-related signal, wherein the first and the second sleep-related signals are indicative of sleep. A sleep detector coupled to the first and the second sensors is configured to adjust a sleep threshold associated with the first sleep-related signal using the second sleep-related signal. The sleep detector detects a sleep condition by comparing the first sleep-related signal with the adjusted threshold. A component of one or more of the sleep detector, first sensor, and second sensor is implantable.

In accordance with another embodiment of the present invention, a method for sleep detection involves adjusting a sleep threshold associated with a first sleep-related signal using a second sleep-related signal. The first sleep-related signal is compared to the adjusted threshold and sleep is detected based on the comparison.

Yet another embodiment of the invention includes means for adjusting a sleep threshold of a first sleep-related signal using a second sleep-related signal, means for comparing the first sleep-related signal to the adjusted threshold, and means for detecting sleep based on the comparison.

In a further embodiment of the invention, a method for detecting sleep includes sensing a plurality of sleep-related signals. A relationship is defined between at least two of the sleep-related signals, the relationship associated with sleep detection. Sleep is detected using the sleep-related signal relationship. At least one of the sensing and detecting is performed at least in part implantably.

The above summary of the invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
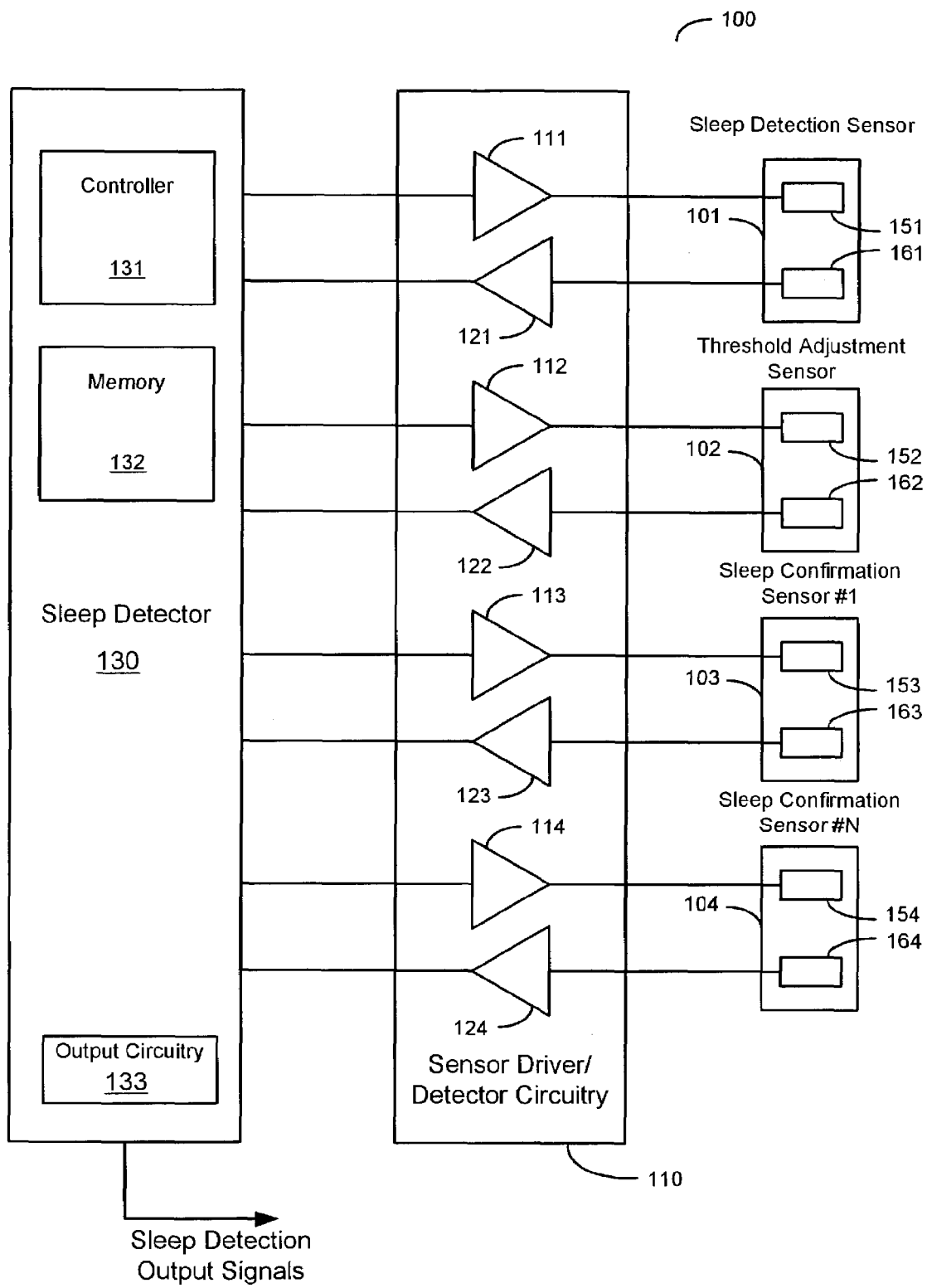
FIG. 1 is a block diagram of a sleep detection device in accordance with an embodiment of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which are shown by way of illustration, various embodiments by which the invention may be practiced. It is to be understood that other embodiments may be utilized, and structural and functional changes may be made without departing from the scope of the present invention.

An adequate duration and quality of sleep is required to maintain sleep-related homeostasis. Prolonged sleep deprivation or periods of poor quality sleep ultimately will have serious health consequences. To diagnose the reasons for sleep disturbances, people suffering from sleep disorders may spend one or more nights in a sleep laboratory. In a sleep laboratory, a patient is typically instrumented for data acquisition and observed by trained personnel. Sleep assessment in a laboratory setting presents a number of obstacles in acquiring an accurate picture of a patient's typical sleep patterns. For example, spending a night in a sleep laboratory typically causes a patient to experience a condition known as "first night syndrome," involving disrupted sleep during the first few nights in an unfamiliar location. Furthermore, sleeping while instrumented and observed may not result in a realistic perspective of the patient's normal sleep patterns.

Sleep quality assessments depend upon acquiring data regarding a patient's typical sleep patterns. An initial step to sleep quality assessment is an accurate and reliable method for recognizing that a patient is asleep. Detecting the onset, termination, duration, stages, and quality of sleep experienced by a patient may be used in connection with the treatment of various conditions. For example, detection of disordered breathing during sleep may be helpful in delivering appropriate therapy for patients suffering from sleep disorders ranging from snoring to sleep apnea. Furthermore, trending sleep data over a long term, including number and severity of disordered breathing episodes, arousal episodes or periods of disturbed sleep, may provide insight into the emotional and physical health of a patient. For example, knowledge of sleep patterns may influence a number of aspects of patient therapy including cardiac or respiratory therapy.

In the context of cardiac rhythm management (CRM) therapy, for example, it may be advantageous to regulate the lower rate limit of a pacemaker based on recognition of sleep or non-sleep states. Adjustment of the lower rate limit to accommodate periods of sleep may improve the quality of the patient's sleep in addition to lengthening battery life of the CRM device. Furthermore, arrhythmia therapy may be improved with sleep recognition. The periods of arousal from REM sleep have been associated with an increased likelihood of arrhythmia for patients with heart disease. Therefore, the ability to recognize sleep may enhance the ability to predict and detect arrhythmias associated with sleep and to provide anti-arrhythmia therapy during sleep.

Respiratory therapy may also be enhanced by a method for accurately recognizing a sleep state. Sleep apnea treatments may include positive airway pressure devices that supply a steady or adjustable flow of air to the patient during sleep, periodic electrical stimulation of the hypoglossal nerve to open the upper airways, and cardiac atrial overdrive pacing to suppress sleep apnea events or awaken the patient to terminate an apneic event. Each of these methods, as well as methods for treating respiratory disorders, may be improved by reliable detection that the patient is sleeping.

Various embodiments of the invention involve detecting sleep using signals associated with a condition of sleep. One embodiment of the invention involves adjusting a sleep threshold associated with a first sleep-related signal using a second sleep-related signal. The first sleep-related signal is compared to the adjusted threshold and sleep is detected based on the comparison. At least one of sensing the sleep-related signals, comparing the first sleep-related signal to the sleep threshold, and detecting sleep is performed at least in part implantably.

Another embodiment of the invention involves defining a relationship between two or more sleep-related signals. The relationship is associated with sleep detection. Sleep is detected using the relationship. Sensing the sleep-related signals and/or detecting sleep is performed at least in part implantably.

Defining a relationship includes, for example, establishing a sleep criterion associated with at least one of the sleep-related signals. The criterion may be, for example, a threshold or other index related to the condition of sleep. Detection of sleep involves comparing the sleep criterion to the state of one or more of the sleep-related signals.

According to one embodiment of the invention, the sleep-related signals may be derived from external or implantable sensors and analyzed by an external sleep detector. Some or all of the sensors may have remote communication capabilities, such as a wireless Bluetooth communications transmitter or transceiver, to link them to the sleep detector.

According to another embodiment of the invention, the sleep-related signals may be derived from external or implantable sensors and analyzed by an implantable device. The sleep detector may be a component of a device that also performs other functions, such as cardiac pacemaker or defibrillation functions. Some or all of the sensors may be wirelessly coupled to the implantable device by telemetry, for example.

According to an embodiment of the present system, methods of sleep detection may be implemented in an implantable cardiac rhythm management (CRM) system configured as a dual chamber pacemaker device which may operate in numerous pacing modes known in the art. The systems and methods of the present invention may also be implemented in various types of implantable or external diagnostic medical devices including, for example, polysomnography devices, respiratory monitors, and cardiac monitors. In addition, the systems and methods of the present invention may be implemented in a number of implantable or external therapeutic medical devices such as continuous positive airway pressure (CPAP) devices or hypoglossal nerve stimulators.

FIG. 1 is a block diagram of a sleep detection device 100 that may be used to detect sleep in accordance with an embodiment of the invention. The sleep detection device includes a number of sensors 101, 102, 103, 104 that sense sleep-related signals associated with sleep. A representative set of sensed sleep-related signals associated with sleep include body movement, heart rate, QT interval, eye movement, respiration rate, transthoracic impedance, tidal volume, minute ventilation, body posture, electroencephalogram (EEG), electrocardiogram (ECG), electrooculogram (EOG), electromyogram (EMG), muscle tone, body temperature, time of day, historical sleep times, blood pressure, and pulse oximetry.

A first sleep-related signal derived from a sleep detection sensor 101 is a signal associated with sleep that is compared to a sleep threshold for detecting the onset and termination of sleep. A second sleep-related signal derived from a threshold adjustment sensor 102 is used to adjust the sleep threshold. Although one sleep detection sensor and one threshold adjustment sensor are shown in FIG. 1, any number of thresholds or other indices corresponding to a number of sleep detection sensors may be used. Furthermore, signals from any number of adjustment sensors may be used to adjust the thresholds or indices of a plurality of sleep detection signals. Additional sleep-related signals derived from confirmation sensors 103, 104 may optionally be used to confirm the onset or termination of the sleep condition.

The sleep-related signals derived from the sensors 101, 102, 103, 104 are received by a sensor driver/detector system 110 which includes detection circuitry 121, 122, 123, 124. The detection circuitry 121, 122, 123, 124 may include, for example, amplifiers, signal processing circuitry, and/or A/D conversion circuitry for each sensor signal. The sensor driver/detector system 110 may further include sensor drive circuitry 111, 112, 113, 114 required to activate the sensors 101, 102, 103, 104.

A sleep detector 130, according to certain embodiments, transmits control signals to the drive circuitry 111, 112, 113, 114 and receives signals from the detection circuitry 121, 122, 123, 124. The sleep detector 130 may include a microprocessor controller 131 which cooperates with memory circuitry 132 for implementing sleep detection methods of the present invention. The memory circuitry 132 may be used to store program data to implement sleep detection, to store parameters associated with sleep detection, such as a sleep threshold, or to store historical data regarding sleep onset and termination over a selected period.

The sleep detector 130 is configured to compare the level of a first sleep-related signal to a sleep threshold adjusted by a second sleep-related signal and determine sleep onset or termination based on the comparison. The sleep detector 130 may use one or more thresholds or indices associated with one or more sleep-related signals. In addition, the sleep detector 130 may use one or more sleep-related signals to adjust the sleep thresholds or indices. Furthermore, the sleep detector 130 may confirm the onset or termination of sleep using an additional number of sleep-related signals.

The sleep detector 130 may include output circuitry 133 for communicating various signals associated with sleep to another device, to other components of a sleep detection device, a data storage device and/or a display device. The signals associated with sleep may include, for example, a sleep detection signal, parameters associated with sleep detection, such as a sleep threshold, and/or historical data relevant to sleep (e.g., historical sleep time data or an average of same which can be used to establish a sleep threshold). The sleep detector may communicate with another device over a wired or wireless communication channel, for example.

The sensors 101, 102, 103, 104 may comprise implantable sensors or external sensors. In one embodiment, the sensors 101, 102, 103, 104 are coupled to the sensor driver/detector circuitry 110 and thus to the sleep detector 130 through a wired connection. In another embodiment, the sensors 101, 102, 103, 104 and sensor driver/detector circuitry 110 are incorporated into sensing devices that include wireless communication capabilities, e.g., a Bluetooth transmitter or transceiver, and may be coupled to the sleep detector 130 through a wireless link. The sleep detector 130 and/or sensor driver/detector circuitry 110 may be incorporated into an implantable or external device.

Figure 2:
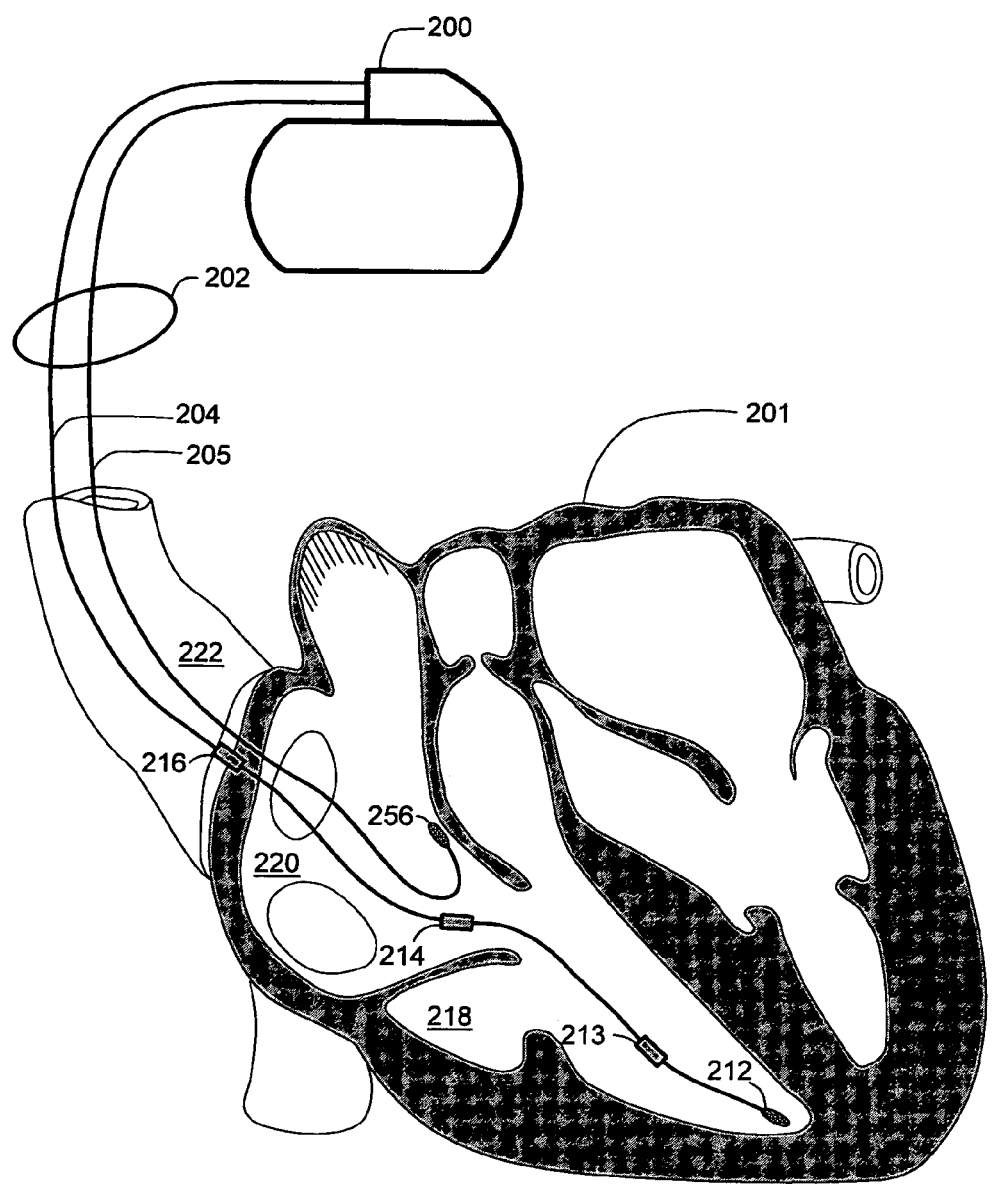
FIG. 2 is a partial view of one embodiment of an implantable medical device that may be used for sleep detection in accordance with an embodiment of the invention.

FIG. 2 is a partial view of one embodiment of an implantable medical device that may be used for sleep detection in accordance with the principles of the invention. The implantable device illustrated in FIG. 2 is a cardiac rhythm management (CRM) system that includes an implantable pacemaker 200 electrically and physically coupled to an intracardiac lead system 202. The intracardiac lead system 202 is implanted in a human body with portions of the intracardiac lead system 202 inserted into a heart 201. The intracardiac lead system 202 is used to detect and analyze electric cardiac signals produced by the heart 201 and to provide electrical energy to the heart 201 under predetermined conditions to treat cardiac arrhythmias of the heart 201.

The CRM 200 depicted in FIG. 2 is a dual chamber device, capable of sensing signals from the right atrium and right ventricle and providing pacing pulses to the right atrium and the right ventricle. Low energy pacing pulses may be delivered to the heart to regulate the heart beat or maintain a lower rate heart beat, for example. In a configuration that includes cardioversion/defibrillation capabilities, high energy pulses may also be delivered to the heart if an arrhythmia is detected that requires cardioversion or defibrillation.

The intracardiac lead system 202 includes a right ventricular lead system 204 and a right atrial lead system 205. The right ventricular lead system 204 includes an RV-tip pace/sense electrode 212 and one or more electrodes 213, 214, 216 suitable for measuring transthoracic impedance. In one arrangement, impedance sense and drive electrodes 216, 214, 213 are configured as ring electrodes. The impedance drive electrode 213 may be located, for example, in the right ventricle 218. The impedance sense electrode 214 may be located in the right atrium 220. Alternatively or additionally, an impedance sense electrode 216 may be located in the superior right atrium 220 or near the right atrium 220 within the superior vena cava 222.

A two-electrode impedance sensing configuration is also possible, wherein the right ventricular lead system includes an impedance drive electrode 213 and a tip electrode 212. In this configuration, the tip electrode 212 may be used as the impedance sense electrode as well as a cardiac sense/pace electrode. Other locations and combinations of impedance sense and drive electrodes are also possible.

The atrial lead system 205 includes an A-tip cardiac pace/sense electrode 256.

In the configuration of FIG. 2, the intracardiac lead system 202 is positioned within the heart 201, with a portion of the atrial lead system 205 extending into the right atrium 220 and portions of the right ventricular lead system 204 extending through the right atrium 220 into the right ventricle 218. The A-tip electrode 256 is positioned at an appropriate location within the right atrium 220 for pacing the right atrium 220 and sensing cardiac activity in the right atrium 220. The RV-tip electrode 212 is positioned at appropriate locations within the right ventricle 218 for pacing the right ventricle 218 and sensing cardiac activity in the right ventricle 218.

Additional configurations of sensing, pacing and defibrillation electrodes can be included in the intracardiac lead system to allow for various sensing, pacing, and defibrillation capabilities of multiple heart chambers. In one configuration, the right ventricular and right atrial leads may include additional electrodes for bipolar sensing and/or pacing, for example. Further, the right ventricular and right atrial leads may also include additional electrodes for cardioversion or defibrillation.

In other configurations, the intracardiac lead system may have only a single lead with electrodes positioned in the right atrium or the right ventricle to implement sleep detection and single chamber cardiac pacing. In yet other embodiments, the intracardiac lead system may include endocardial leads that are advanced into the coronary sinus and coronary veins to locate the distal electrode(s) adjacent to the left ventricle or the left atrium.

Other intracardiac lead and electrode arrangements and configurations known in the art are also possible and considered to be within the scope of the present system.

Figure 3:
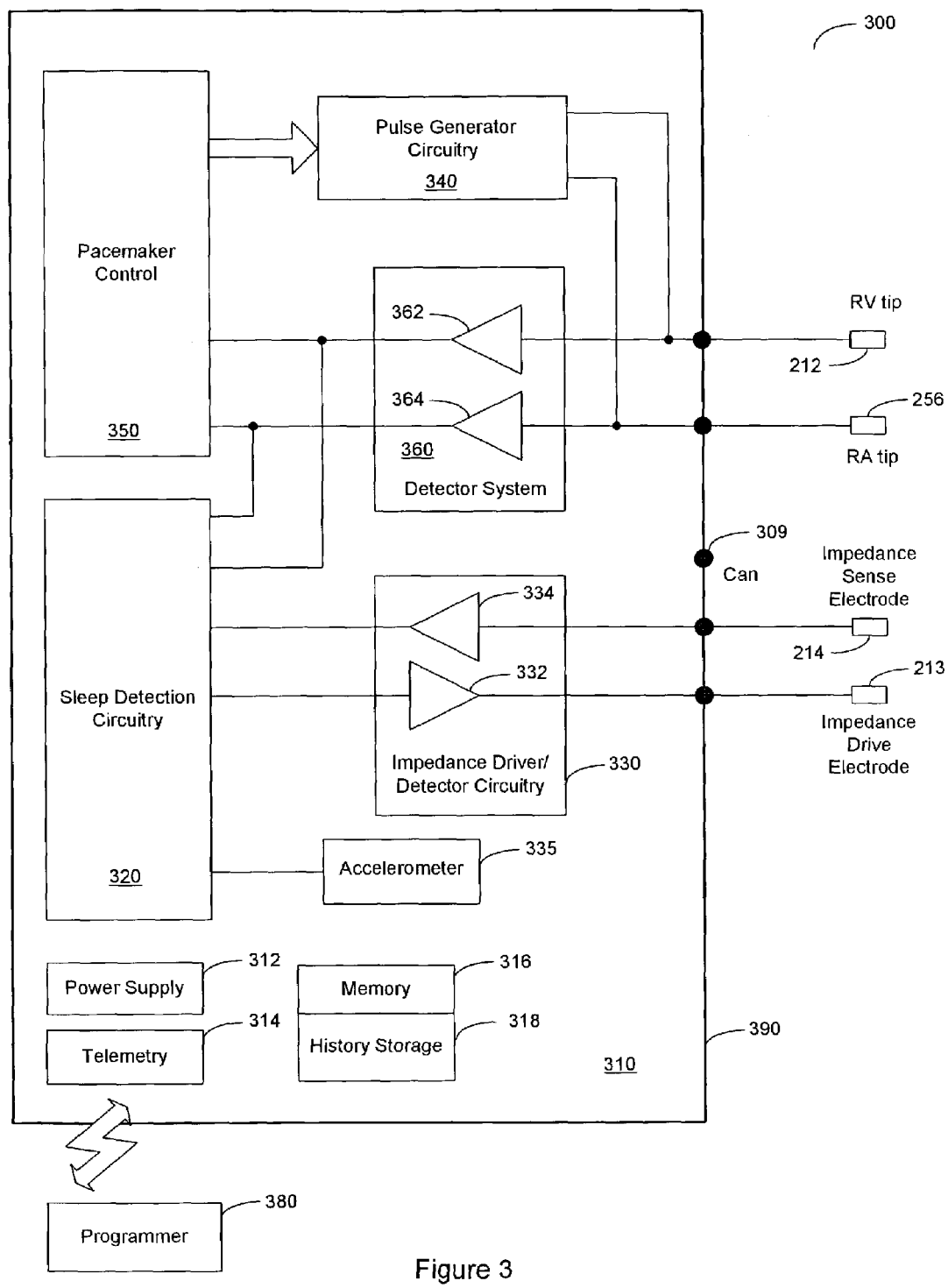
FIG. 3 is a system block diagram of an implantable medical device with which sleep detection may be implemented in accordance with an embodiment of the invention.

Referring now to FIG. 3, there is shown a block diagram of an embodiment of a CRM system 300 configured as a pacemaker and suitable for implementing a sleep detection methodology of the present invention. FIG. 3 shows the CRM 300 divided into functional blocks. It will be understood by those skilled in the art that there exist many possible configurations in which these functional blocks can be arranged and implemented. The example depicted in FIG. 3 is one possible functional arrangement. The CRM 300 includes sleep detection circuitry 320 for receiving sleep-related signals and detecting sleep in accordance with an embodiment of the invention.

In one embodiment, sleep detection circuitry 320 is incorporated as part of the CRM circuitry 310 encased and hermetically sealed in a housing 390 suitable for implanting in a human body. Power to the CRM 300 is supplied by an electrochemical battery power supply 312 housed within the CRM 300. A connector block (not shown) is additionally attached to the CRM housing 390 to allow for the physical and electrical attachment of the intracardiac lead system conductors to the CRM circuitry 310.

The CRM circuitry 310 may be configured as a programmable microprocessor-based system, with circuitry for detecting sleep in addition to providing pacing therapy to the heart. Cardiac signals may be detected by the detector circuitry 360 and delivered to the pacemaker control system 350. Pace pulses controlled by the pacemaker control 350 and generated by the pulse generator 340 are delivered to the heart to treat various arrhythmias of the heart.

The memory circuit 316 may store parameters for various device operations involved in sleep detection and/or cardiac pacing and sensing. The memory circuit 316 may also store data indicative of sleep-related signals received by components of the CRM circuitry 310, such as the impedance drive/sense circuitry 330, the cardiac signal detector system 360, and the accelerometer 335.

The sleep detection circuitry 320 receives signals derived from the cardiac signal detector system 360, the impedance driver/detector circuitry 330 and the accelerometer 335 to perform operations involving detecting sleep onset and termination according to the principles of the present invention. Historical data storage 318 may be coupled to the sleep detection circuitry 320 for storing historical sleep related data. Such data may be transmitted to an external programmer unit 380 and used for various diagnostic purposes and as needed or desired.

Telemetry circuitry 314 is coupled to the CRM circuitry 310 to allow the CRM 300 to communicate with an external programmer unit 380. In one embodiment, the telemetry circuitry 314 and the programmer unit 380 use a wire loop antenna and a radio frequency telemetric link to receive and transmit signals and data between the programmer unit 380 and telemetry circuitry 314. In this manner, programming commands and data are transferred between the CRM circuitry 310 and the programmer unit 380 during and after implant.

The programming commands allow a physician to set or modify various parameters used by the CRM. These parameters may include setting sleep detection parameters for use during sleep detection, such as which sleep-related signals are to be used for sleep detection and threshold adjustment, and the initial sleep detection thresholds. In addition, the CRM system 300 may download to the programmer unit 380 stored data pertaining to sensed sleep periods, including the amount of time spent sleeping, the time of day sleep periods occurred, historical data on sleep times, and the number of arousals during the sleep periods, for example.

Signals associated with patient activity and posture may be detected through the use of an accelerometer 335 positioned within the housing 390 of the CRM 300. The accelerometer responds to patient activity and the accelerometer signal may be correlated with activity level, workload and/or posture. Signals derived from the accelerometer 335 are coupled to the sleep detection circuitry 320 and may also be used by the pacemaker circuitry for implementing a rate adaptive pacing regimen, for example.

The impedance sense electrode 214, the impedance drive electrode 213, and the impedance driver/detector circuitry 330 are used to detect a voltage signal related to transthoracic impedance. The transthoracic impedance measurement may be used to calculate various parameters associated with respiration. Under the control of the sleep detection circuitry 320, the impedance driver circuitry 332 produces a current that flows through the blood between the impedance drive electrode 213 and the can electrode 309. The voltage at the impedance sense electrode 214 relative to the can electrode 309 changes as the transthoracic impedance changes. The voltage signal developed between the impedance sense electrode 214 and the can electrode 309 is detected by the impedance sense amplifier 334 located within the impedance driver/detector circuitry 330 and is delivered to the sleep detection circuitry 320 for further processing.

Figure 4:
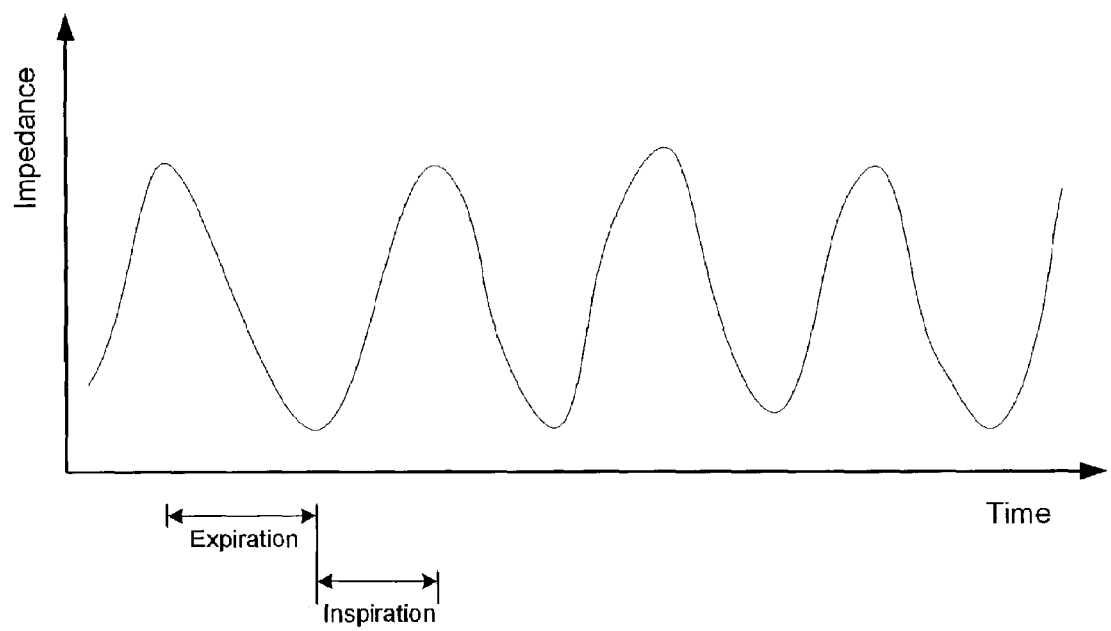
FIG. 4 is a graph of blood impedance used in connection with sleep detection according to an embodiment of the invention.

The voltage signal developed at the impedance sense electrode 214, illustrated in FIG. 4, is proportional to the transthoracic impedance, with the impedance increasing during respiratory inspiration and decreasing during respiratory expiration. The peak-to-peak transition of the impedance measurement, illustrated in FIG. 4, is proportional to the amount of air inhaled in one breath, denoted the tidal volume. The impedance measurement may be further processed to determine the tidal volume, corresponding to the volume of air moved in a breath, or minute ventilation corresponding to the amount of air moved per minute.

In addition to impedance and accelerometer measurements, cardiac signals indicative of heart rate or other cardiac functions may also be used in connection with sleep detection. Turning back to FIG. 3, cardiac signals are sensed through use of the RV-tip and RA-tip sense electrodes 212, 256. More particularly, the right ventricle signal may be detected as a voltage developed between the RV-tip electrode 212 and the can electrode 309. Right ventricle cardiac signals are sensed and amplified by a right ventricle V-sense amplifier 362 located in the detector system 360. The output of the right ventricle V-sense amplifier 362 may be coupled, for example, to a signal processor and A/D converter within the detector system 360. The processed right ventricle signals may be delivered to the pacemaker control 350 and the sleep detection circuitry 320.

Right atrium cardiac signals are sensed and amplified by a right atrial A-sense amplifier 364 located in the detector system 360. The output of the right atrium A-sense amplifier 364 may be processed by signal processing circuitry and received by the pacemaker control 350 and the sleep detection circuitry 320.

The pacemaker control 350 communicates pacing control signals to the pulse generator circuitry 340 for delivering pacing stimulation pulses to the RV-tip and RA-tip electrodes 212 and 256, respectively, according to a preestablished pacing regimen under appropriate conditions.

Figure 5:
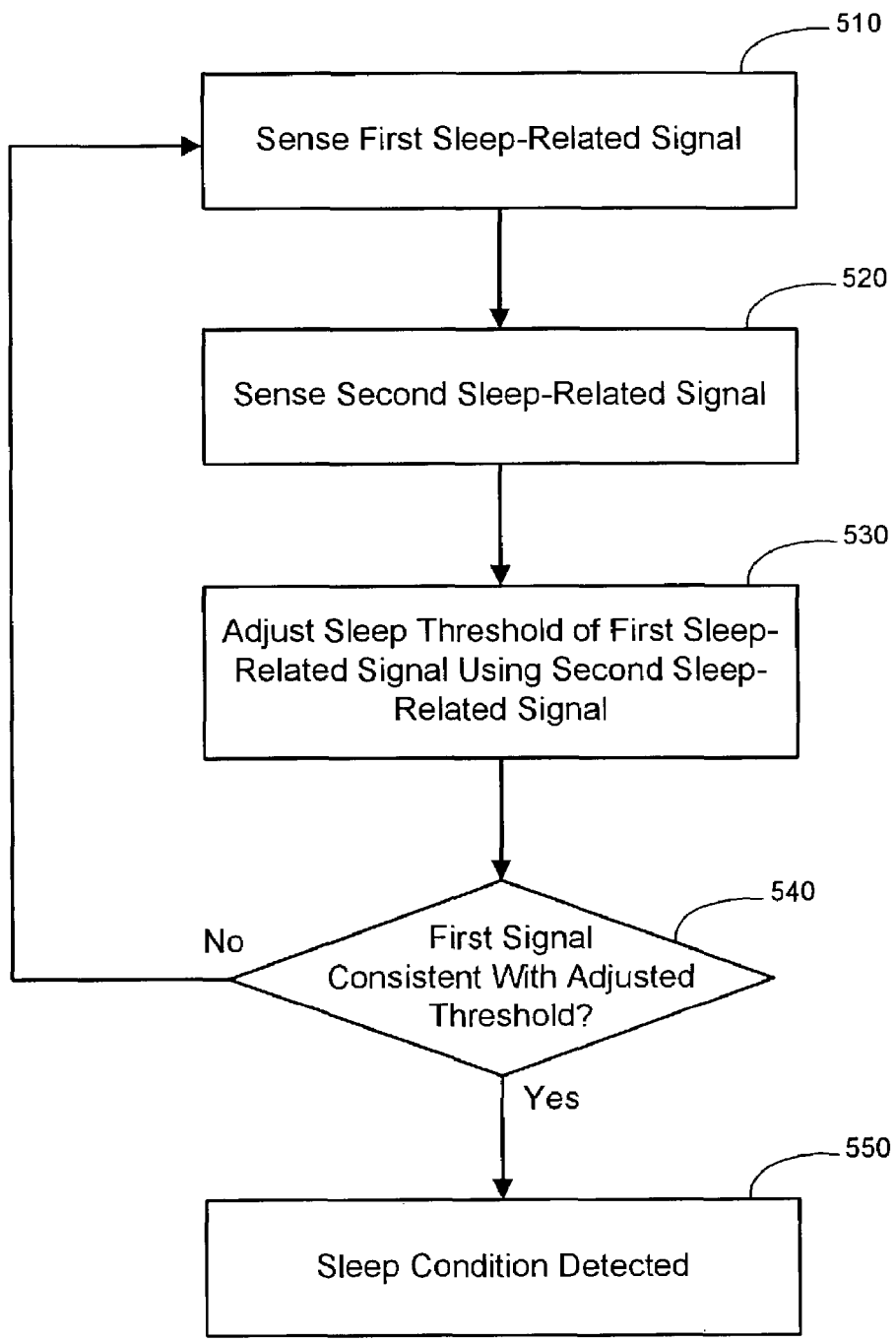
FIG. 5 is a flow graph illustrating a method of detecting sleep according to an embodiment of the invention.

FIG. 5 illustrates a method of detecting sleep according to principles of the invention. A sleep threshold associated with a first sleep-related signal is established. The sleep threshold may be determined from clinical data of a sleep threshold associated with sleep acquired using a group of subjects, for example. The sleep threshold may also be determined using historical data taken from the particular patient for whom the sleep condition is to be detected. For example, a history of a given patient's sleep times can be stored, and a sleep threshold can be developed using data associated with the patient's sleep time history.

The first sleep-related signal is sensed 510. A second sleep-related signal associated with sleep is sensed 520. The first and the second sleep-related signals may be sensed from sensors implanted in the patient, attached externally to the patient or located nearby the patient, for example. The first and the second sleep-related signals may be any signal associated with the condition of sleep, such as the representative sleep-related signals associated with sleep listed above.

The sleep threshold established for the first sleep-related signal is adjusted using the second sleep-related signal 530. For example, if the second sleep-related signal indicates a high level of activity that is incompatible with a sleep state, the sleep threshold of the first sleep-related signal may be adjusted downward to require sensing a decreased level of the first sleep-related signal before a sleep condition is detected.

If the first sleep-related signal is consistent with sleep according to the adjusted sleep threshold 540, a sleep condition is detected 550. If the first sleep-related signal is not consistent with sleep using the adjusted sleep threshold, the first and the second sleep-related signals continue to be sensed 510, 520 and the threshold adjusted 530 until a condition of sleep is detected 550.

Figure 6:
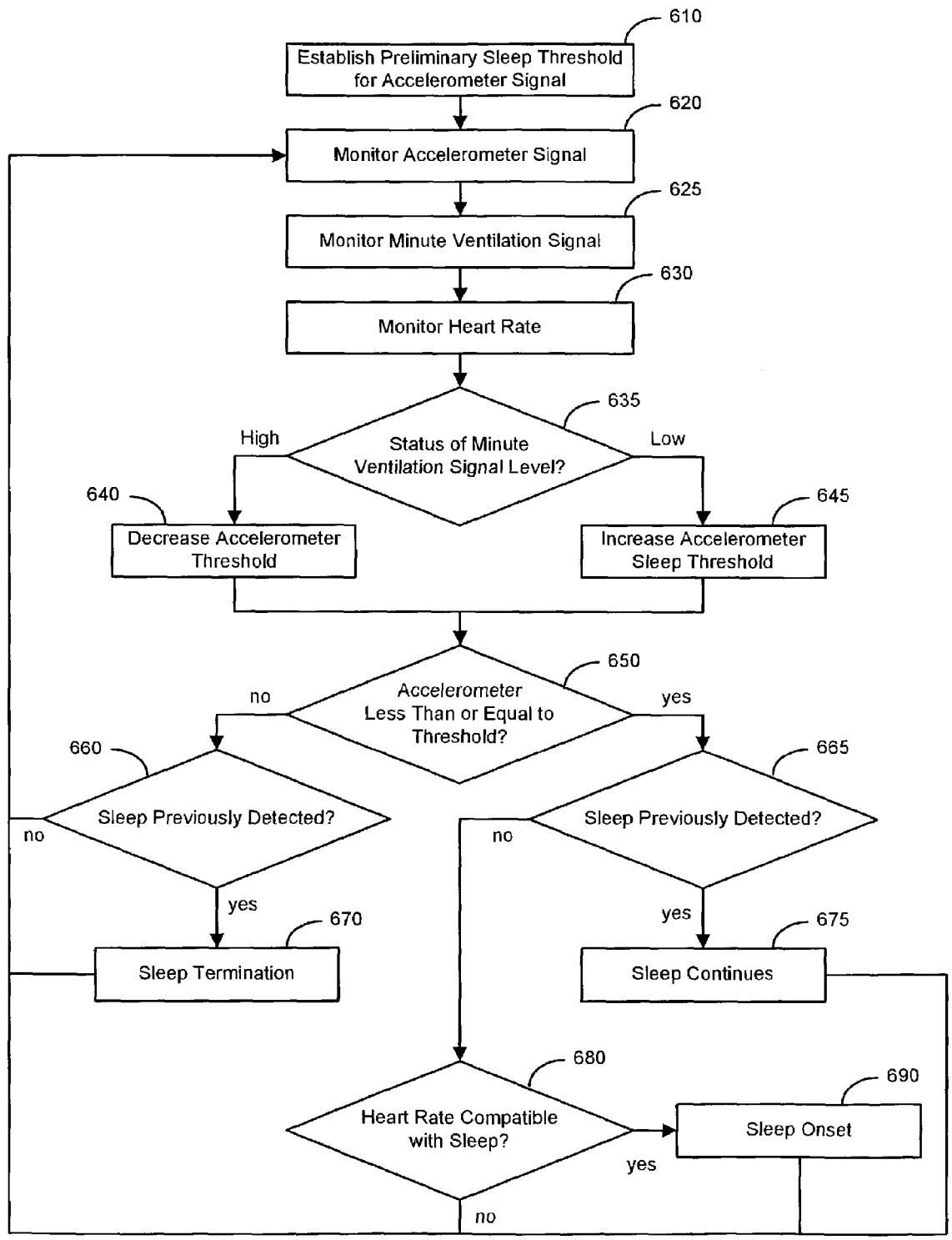
FIG. 6 is a flow graph illustrating a method of detecting sleep using an accelerometer and a minute ventilation sensor according to an embodiment of the invention.

In another embodiment of the invention, illustrated in FIG. 6, an accelerometer and a minute ventilation sensor are used as first and second signals associated with sleep. A preliminary accelerometer signal sleep threshold is determined 610. For example, the preliminary sleep threshold may be determined from clinical data taken from a group of subjects or historical data taken from the patient over a period of time.

The activity level of the patient is monitored using an accelerometer 620 that may be incorporated into an implantable cardiac pacemaker as described above. Alternatively, the accelerometer may be attached externally to the patient. The patient's minute ventilation (MV) signal is monitored 625. The MV signal may be acquired, for example, using the transthoracic impedance method described above using an implantable cardiac device. Other methods of determining the MV signal are also possible and are considered to be within the scope of this invention.

In this example, the accelerometer signal represents the sleep detection signal associated with the sleep threshold. The MV signal is the threshold adjustment signal used to adjust the sleep threshold. Heart rate is monitored 630 in this example to provide a sleep confirmation signal.

Threshold adjustment may be accomplished by using the patient's MV signal to moderate the accelerometer sleep threshold. If the patient's MV signal is low relative to an expected MV level associated with sleep, the accelerometer sleep threshold is increased. Similarly, if the patient's MV signal level is high relative to an expected MV level associated with sleep, the accelerometer sleep threshold is decreased. Thus, when the patient's MV level is high, less activity is required to make the determination that the patient is sleeping. Conversely when the patient's MV level is relatively low, a higher activity level may result in detection of sleep. The use of two sleep-related signals to determine a sleep condition enhances the accuracy of sleep detection over previous methods using only one sleep-related signal to determine that a patient is sleeping.

Various signal processing techniques may be employed to process the raw sensor signals. For example, a moving average of a plurality of samples of each sleep-related signal may be calculated and used as the sleep-related signal. Furthermore, the sleep-related signals may be filtered and/or digitized. If the MV signal is high 635 relative to an expected MV level associated with sleep, the accelerometer sleep threshold is decreased 640. If the MV signal is low 635 relative to an expected MV level associated with sleep, the accelerometer sleep threshold is increased 645.

If the sensed accelerometer signal is less than or equal to the adjusted sleep threshold 650, and if the patient is not currently in a sleep state 665, then the patient's heart rate is checked 680 to confirm the sleep condition. If the patient's heart rate is compatible with sleep 680, then sleep onset is determined 690. If the patient's heart rate is incompatible with sleep, then the patient's sleep-related signals continue to be monitored.

If the accelerometer signal is less than or equal to the adjusted sleep threshold 650 and if the patient is currently in a sleep state 665, then a continuing sleep state is determined and the patient's sleep-related signals continue to be monitored for sleep termination to occur.

If the accelerometer signal is greater than the adjusted sleep threshold 650 and the patient is not currently in a sleep state 660, then the patient's sleep-related signals continue to be monitored until sleep onset is detected 690. If the accelerometer signal is greater than the adjusted sleep threshold 650 and the patient is currently in a sleep state 660, then sleep termination is detected 670.

Figure 7A:
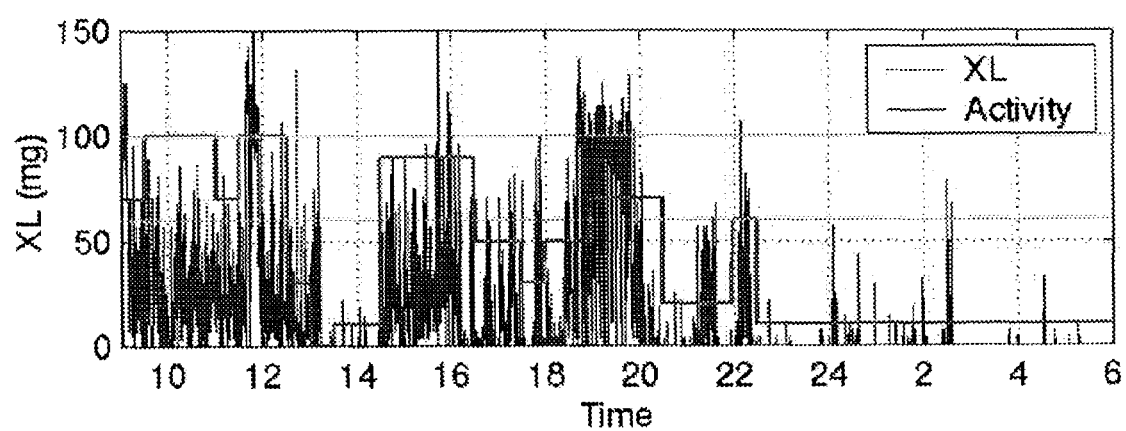
FIG. 7A is a graph of an accelerometer signal indicating patient activity over time that may be used to implement a sleep detection method in accordance with an embodiment of the present invention.
Figure 7B:
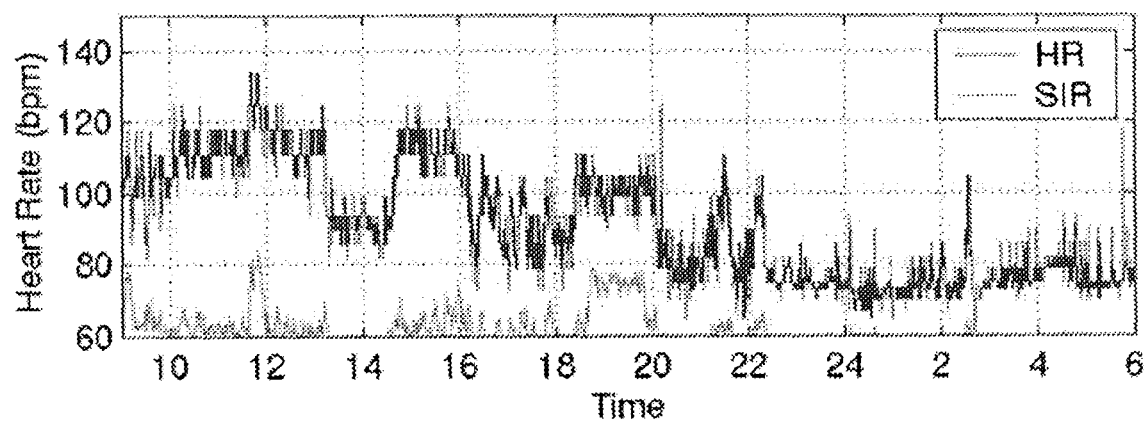
FIG. 7B is a graph of a heart rate signal indicating patient activity over time that may be used to implement a sleep detection method in accordance with an embodiment of the present invention.
Figure 8:
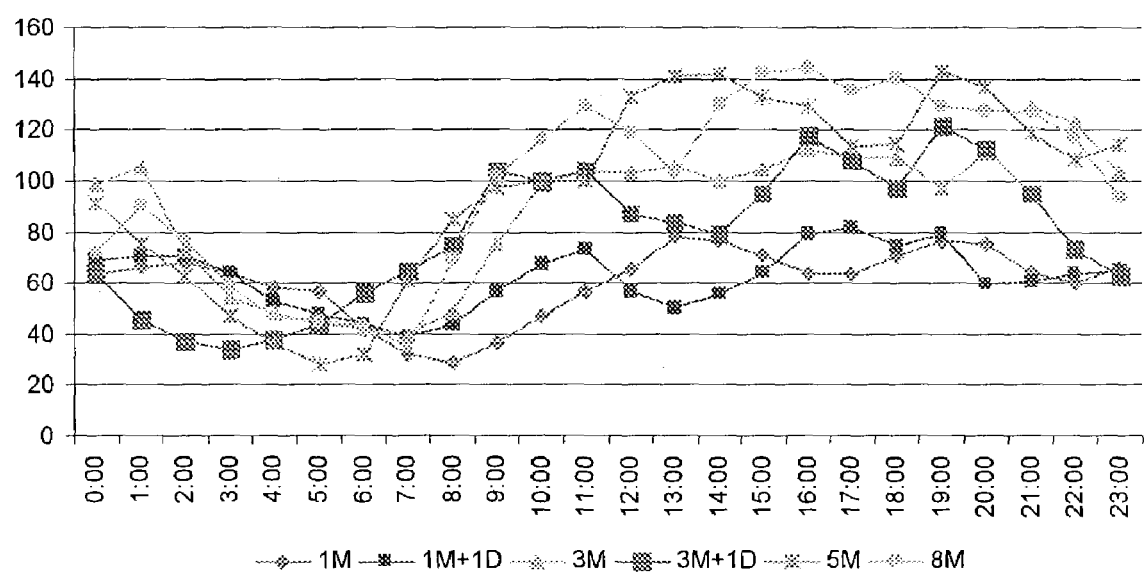
FIG. 8 is a graph of a minute ventilation signal indicating patient respiration that may be used to implement a sleep detection method in accordance with an embodiment of the present invention.
Figure 9:
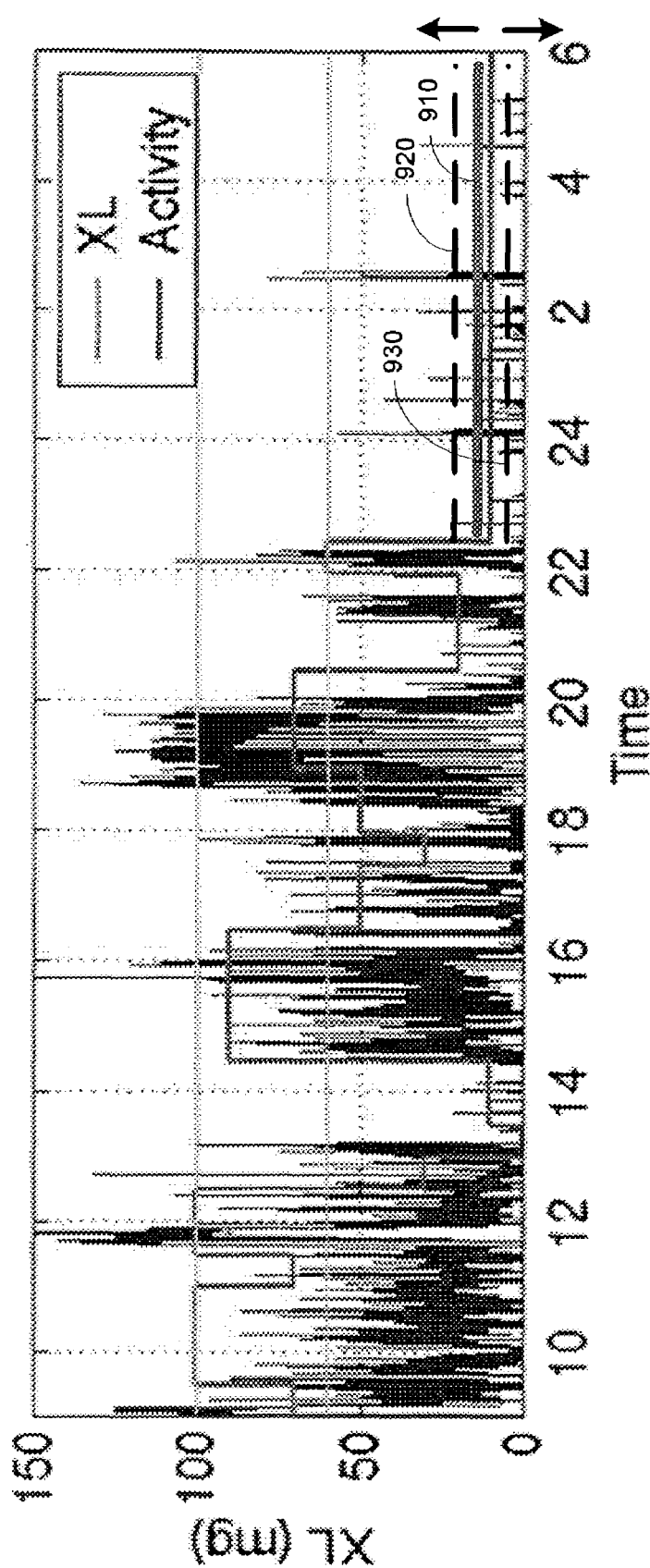
FIG. 9 is a graph illustrating adjustment of an accelerometer sleep threshold using an MV signal in accordance with an embodiment of the invention.

The graphs of FIGS. 7–9 illustrate the adjustment of the accelerometer sleep threshold using the MV signal. The relationship between patient activity and the accelerometer and MV signals is trended over a period of time to determine relative signal levels associated with a sleep condition. FIG. 7A illustrates activity as indicated by the accelerometer signal. The patient's heart rate for the same period is graphed in FIG. 7B. The accelerometer signal indicates a period of sleep associated with a relatively low level of activity beginning at slightly before 23:00 and continuing through 6:00. Heart rate appropriately tracks the activity level indicated by the accelerometer indicating a similar period of low heart rate corresponding to sleep. The accelerometer trends are used to establish a threshold for sleep detection.

FIG. 8 is a graph of baseline trending for an MV signal. Historical data of minute ventilation of a patient is graphed over an 8 month period. The MV signal trending data is used to determine the MV signal level associated with sleep. In this example, a composite MV signal using the historical data indicates a roughly sinusoidal shape with the relatively low MV levels occurring approximately during the period from hours 21:00 through 8:00. The low MV levels are associated with periods of sleep. The MV signal level associated with sleep is used to implement sleep threshold adjustment.

FIG. 9 illustrates adjustment of the accelerometer sleep threshold using the MV signal. The initial sleep threshold 910 is established using the baseline accelerometer signal data acquired as discussed above. If the patient's MV signal is low relative to an expected MV level associated with sleep, the accelerometer sleep threshold is increased 920. If the patient's MV signal level is high relative to an expected MV level associated with sleep, the accelerometer sleep threshold is decreased 930. When the patient's MV level is high, less activity detected by the accelerometer is required to make the determination that the patient is sleeping. However, if the patient's MV level is relatively low, a higher activity level may result in detection of sleep. The use of two sleep-related signals to adjust a sleep threshold for determining a sleep condition enhances the accuracy of sleep detection over previous methods.

Additional sleep-related signals may be sensed and used to improve the sleep detection mechanism described above. For example, a posture sensor may be used to detect the posture of the patient and used to confirm sleep. If the posture sensor indicates a vertical posture, then the posture sensor signal may be used to override a determination of sleep using the sleep detection and threshold adjustment signals. Other signals may also be used in connection with sleep determination or confirmation, including the representative set of sleep-related signals associated with sleep indicated above.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A method of detecting sleep, comprising:
adjusting a sleep threshold associated with a first sleep-related signal using a second sleep-related signal;
comparing the first sleep-related signal to the adjusted threshold; and
detecting sleep based on the comparison, wherein at least one of adjusting, comparing or detecting steps is performed at least in part implantably.

2. The method of claim 1, wherein at least one of the first or the second sleep-related signals is a physiological signal.

3. The method of claim 1, further comprising establishing the sleep threshold associated with the first sleep-related signal.

4. The method of claim 3, wherein the sleep threshold is established based on clinical data.

5. The method of claim 3, wherein the sleep threshold is established using the first sleep-related signal.

6. The method of claim 3, wherein the sleep threshold is established using data associated with historical sleep times.

7. The method of claim 1, wherein detecting sleep based on the comparison comprises:
detecting sleep onset if the first sleep-related signal falls below the adjusted threshold; and
detecting sleep termination if the first sleep-related signal rises above the adjusted threshold.

8. The method of claim 1, wherein the first sleep-related signal is associated with patient activity.

9. The method of claim 1, wherein the first sleep-related signal is an accelerometer signal.

10. The method of claim 1, wherein the first sleep-related signal is sensed using an implantable sensor.

11. The method of claim 1, wherein the first sleep-related signal is sensed using an external sensor.

12. The method of claim 1, wherein the second sleep-related signal is associated with patient respiration.

13. The method of claim 1, wherein the second sleep-related signal comprises transthoracic impedance.

14. The method of claim 1, wherein the second sleep-related comprises minute ventilation.

15. The method of claim 1, wherein the second sleep-related signal comprises tidal volume.

16. The method of claim 1, wherein the second sleep-related signal is associated with cardiac function.

17. The method of claim 1, wherein the second sleep-related signal comprises a QT interval signal.

18. The method of claim 1, wherein the second sleep-related signal is sensed using an implantable sensor.

19. The method of claim 1, wherein the second sleep-related signal is sensed using an external sensor.

20. The method of claim 1, wherein detecting sleep comprises detecting sleep using an implantable device.

21. The method of claim 20, wherein the implantable device is an implantable pulse generator.

22. The method of claim 1, wherein detecting sleep comprises detecting sleep using an external device.

23. The method of claim 1, wherein detecting sleep further comprises confirming sleep using a third sleep-related signal.

24. The method of claim 1, wherein detecting sleep further comprises:
comparing a third sleep-related signal to a predetermined value; and
confirming sleep based on the comparison.

25. The method of claim 24, wherein the third sleep-related signal comprises a posture detector signal.

26. The method of claim 24, wherein the third sleep-related signal comprises a body temperature signal.

27. The method of claim 24, wherein the third sleep-related signal comprises an EOG signal.

28. The method of claim 24, wherein the third sleep-related signal comprises an EEG signal.

29. The method of claim 24, wherein the third sleep-related signal comprises an EMG signal.

30. The method of claim 24, wherein the third sleep-related signal comprises a respiration signal.

31. The method of claim 24, wherein the third sleep-related signal comprises a cardiac signal.

32. The method of claim 24, wherein the third sleep-related signal comprises a blood pressure signal.

33. A sleep detection device, comprising:
a first sensor configured to sense a first sleep-related signal;
a second sensor configured to sense a second sleep-related signal; and
a sleep detector coupled to the first and the second sensors and configured to adjust a sleep threshold associated with the first sleep-related signal using the second sleep-related signal, and to detect a sleep condition by comparing the first sleep-related signal with the adjusted threshold, wherein one of the first sensor, second sensor and sleep detector comprises an implantable component.

34. The device of claim 33, wherein the sleep threshold is established based on clinical data.

35. The device of claim 33, wherein the sleep detector is further configured to establish the sleep threshold using the first sleep-related signal.

36. The device of claim 33, wherein the sleep detector is configured to detect sleep onset if the first sleep-related signal falls below the adjusted threshold and detect sleep termination if the first sleep-related signal rises above the adjusted threshold.

37. The device of claim 33, wherein the first sleep-related signal is associated with patient activity.

38. The device of claim 33, wherein the first sleep-related signal comprises a cardiac signal.

39. The device of claim 33, wherein the first sleep-related signal comprises a respiration signal.

40. The device of claim 33, wherein the first sleep-related signal comprises an accelerometer signal.

41. The device of claim 33, wherein the first sleep-related signal is derived from an implantable sensor.

42. The device of claim 33, wherein the first sleep-related signal is derived from an external sensor.

43. The device of claim 33, wherein the second sleep-related signal comprises a cardiac signal.

44. The device of claim 33, wherein the second sleep-related signal comprises a respiration signal.

45. The device of claim 33, wherein the second sleep-related signal comprises a transthoracic impedance signal.

46. The device of claim 33, wherein the second sleep-related signal comprises a minute ventilation signal.

47. The device of claim 33, wherein the second sleep-related signal is derived from an implantable sensor.

48. The device of claim 33, wherein the second sleep-related signal is derived from an external sensor.

49. The device of claim 33, wherein the sleep detector comprises an implantable device.

50. The device of claim 33, wherein the sleep detector comprises an external device.

51. The device of claim 33, wherein the sleep detector is configured as a component of a pulse generator.

52. The device of claim 33, wherein the sleep detector is configured as a component of a therapeutic device.

53. The device of claim 33, wherein the sleep detector is configured as a cardiac pacemaker.

54. The device of claim 33, wherein the sleep detector is configured as a component of a patient monitoring device.

55. The device of claim 33, further comprising:
a third sensor to sense a third sleep-related signal; and
wherein the sleep detector is further configured to compare the third sleep-related signal with a threshold and to confirm a sleep condition based on the comparison.

56. The device of claim 55, wherein the third sleep-related signal comprises a cardiac signal.

57. The device of claim 55, wherein the third sleep-related signal comprises a respiration signal.

58. The device of claim 55, wherein the third sleep-related signal comprises a body temperature signal.

59. The device of claim 55, wherein the third sleep-related signal comprises a blood pressure signal.

60. The device of claim 33, wherein the sleep threshold is established using data associated with historical sleep times.

61. A system for detecting sleep, comprising:
means for adjusting a sleep threshold associated with a first sleep-related signal using a second sleep-related signal;
means for comparing the first sleep-related signal to the adjusted threshold; and
means for detecting sleep based on the comparison,
wherein one of the means for adjusting, comparing or detecting comprises an implantable component.

62. The system of claim 61, further comprising means for establishing the sleep threshold associated with the first sleep-related signal.

63. The system of claim 61, further comprising:
means for sensing a third sleep-related signal;
means for comparing the third sleep-related signal to a predetermined value; and
means for confirming sleep based on the comparison.

* * * * *

UNITED STATES PATENT AND TRADEMARK OFFICE
CERTIFICATE OF CORRECTION

PATENT NO. : 7,189,204 B2  
APPLICATION NO. : 10/309771  
DATED : March 13, 2007  
INVENTOR(S) : Ni et al.

Page 1 of 1

It is certified that error appears in the above-identified patent and that said Letters Patent is hereby corrected as shown below:

In the Claims:

Col. 12, line 20: "sleep-related comprises" should read --sleep-related signal comprises--.

Signed and Sealed this

Twenty-sixth Day of February, 2008

JON W. DUDAS  
*Director of the United States Patent and Trademark Office*